United States Patent

Pleznac

[11] 3,941,129
[45] Mar. 2, 1976

[54] QUANTITY INDICATING INJECTION DEVICE

[76] Inventor: Ida M. Pleznac, 7837 Manor Blvd., Dearborn, Mich. 48126

[22] Filed: Dec. 10, 1974

[21] Appl. No.: 531,212

[52] U.S. Cl. .......... 128/218 R; 128/272; 128/218 P; 128/218 PA; 128/215; 222/309; 222/137
[51] Int. Cl.² .................. A61J 1/00; A61M 5/315
[58] Field of Search ............ 128/272, 218 R, 218 P, 128/218 PA, 276, 215; 222/309, 23, 41, 137; 116/124 A, 130, 135

[56] References Cited
UNITED STATES PATENTS

| | | | |
|---|---|---|---|
| 2,591,706 | 4/1952 | Lockhart | 128/218 D |
| 2,665,687 | 1/1954 | Brown | 128/272 X |
| 3,248,014 | 4/1966 | Gill | 222/137 |
| 3,259,130 | 7/1966 | Kauthamer | 128/218 R |
| 3,359,979 | 12/1967 | Murdoch | 128/218 R |
| 3,618,603 | 11/1971 | Levenson | 128/218 P |

FOREIGN PATENTS OR APPLICATIONS
918,100  2/1963  United Kingdom................. 128/272

Primary Examiner—Aldrich F. Medbery

[57] ABSTRACT

A cartridge or injecting device for storing and dispensing medical solutions, such cartridge being characterized by a tubular member with a needle on one end having an opening therethrough communicating with the interior of the tubular member. A slidable drive stopper in the other end of the tubular member has thereon an elongated plunger for advancing and retracting the drive stopper. A non-retractable stopper in the tubular member, in contact with the forward end of the drive stopper, has therethrough a longitudinal opening. The non-retractable stopper is therefore shifted forwardly when the drive stopper is advanced thus serving as a visual indicator showing that medical solution has been ejected from the cartridge.

5 Claims, 18 Drawing Figures

U.S. Patent  March 2, 1976  Sheet 1 of 2  3,941,129
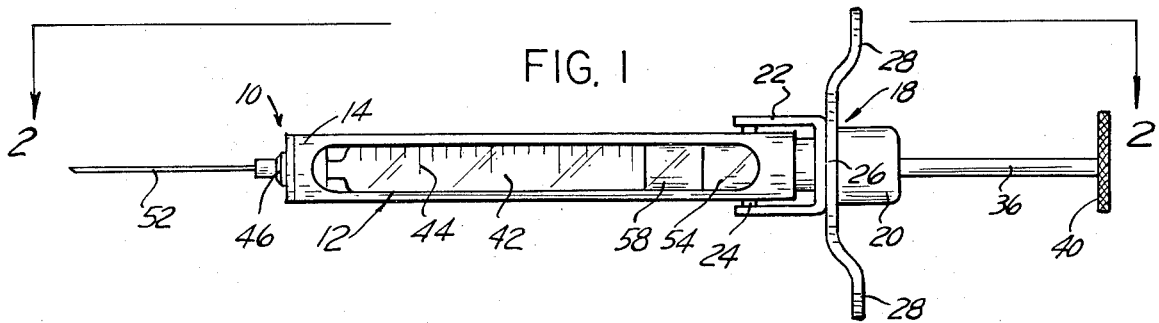
FIG. 1
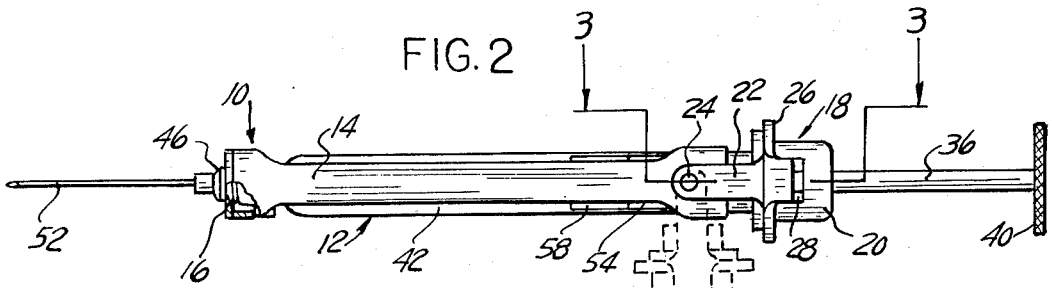
FIG. 2
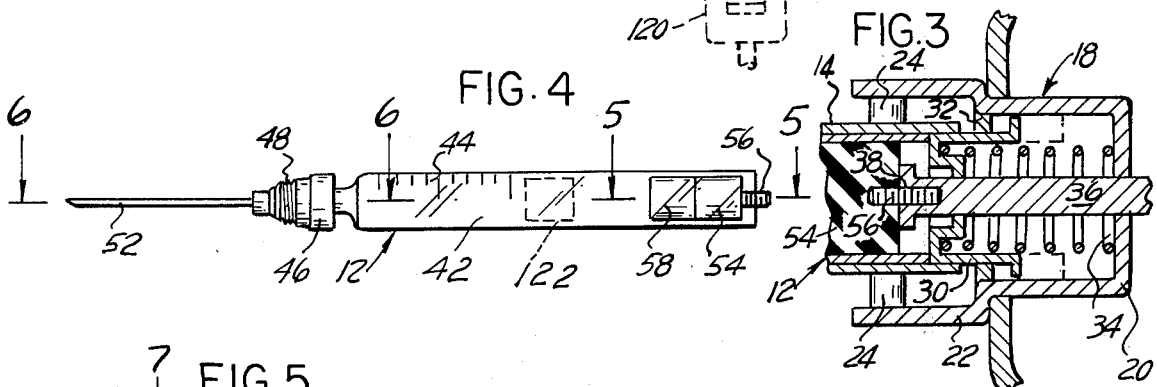
FIG. 4    FIG. 3
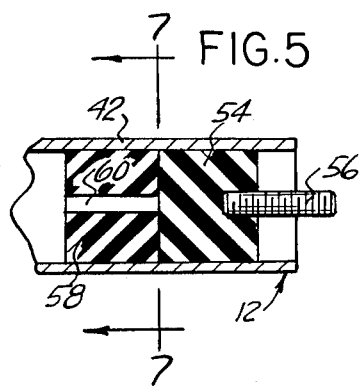
FIG. 5
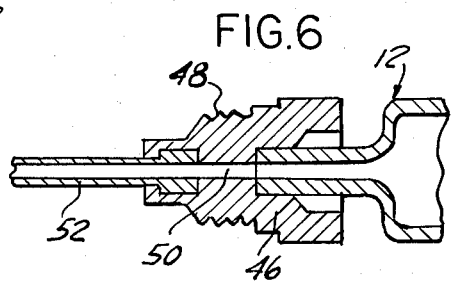
FIG. 6
FIG. 7
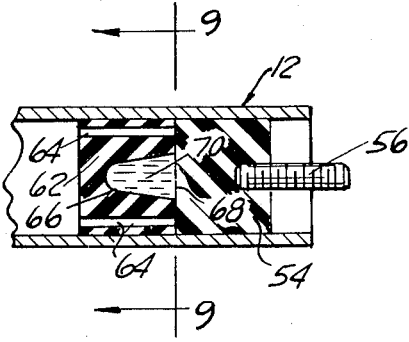
FIG. 8
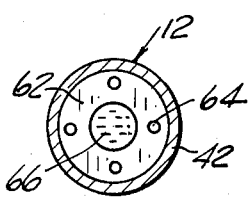
FIG. 9
INVENTOR
IDA M. PLEZNAC
BY Adolph G. Martin
ATTORNEY

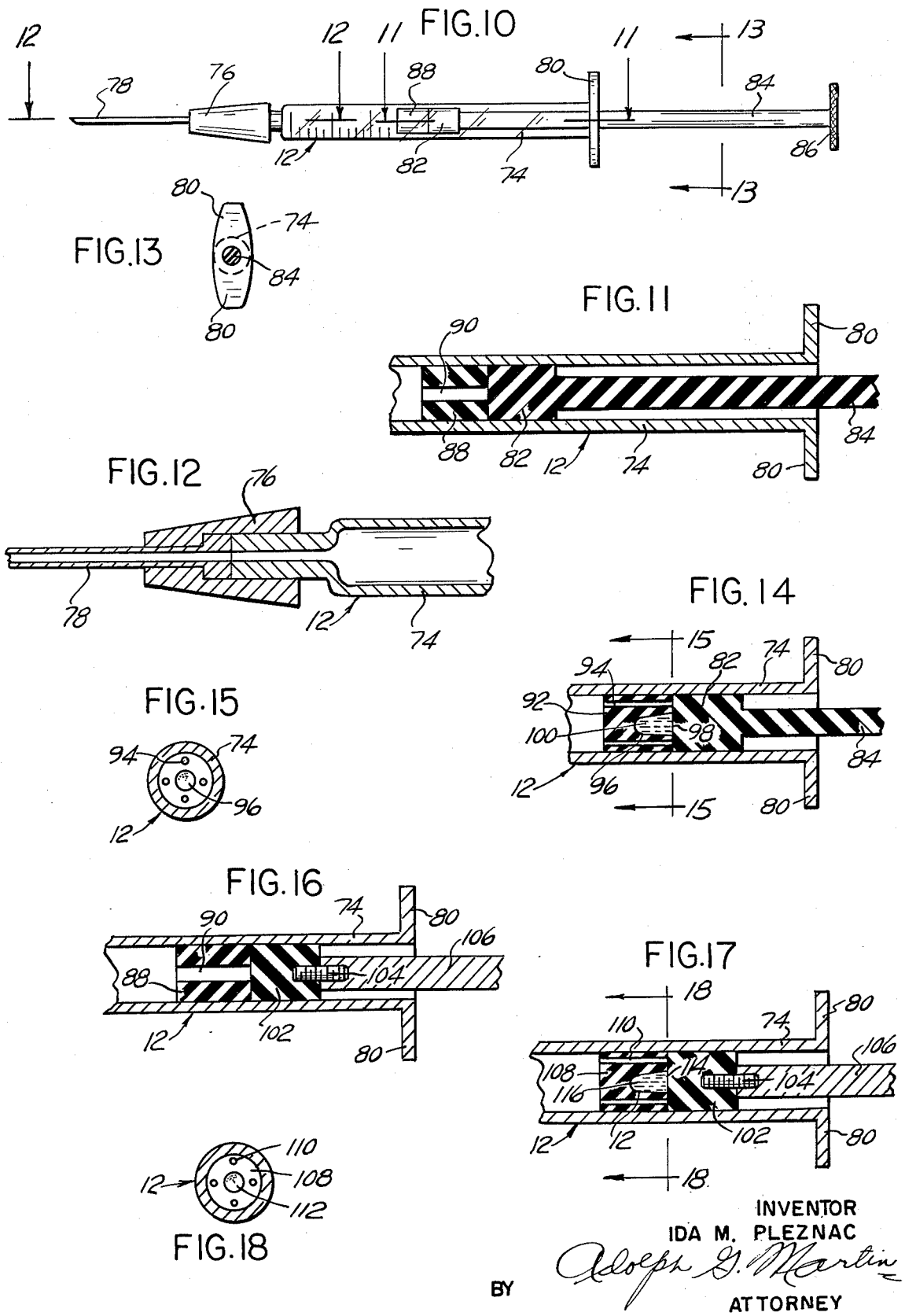

QUANTITY INDICATING INJECTION DEVICE

BACKGROUND OF THE INVENTION

This invention relates generally to cartridges for medical solutions, but more particularly to a cartridge of the type adapted for use in storing and dispensing narcotics. Presently, cartridges containing narcotics for medical use have no effective safe-guards to prevent dilution of the contents, not a means for indicating the amount of original solution in the cartridge that has been withdrawn. Consequently, a large portion of the narcotic solutions administered in the course of patient therapy has been diluted by the personnel in our institutions and professional offices. Therefore, many patients suffer severely as a result of receiving less than the prescribed dosages of pain depressants, and accordingly pay for medications which are never administered to them. For this reason, the applicant has designed a cartridge which will accurately indicate the amount of original solution which has been withdrawn.

SUMMARY OF THE INVENTION

The broadest concept of this invention is disclosed in FIGS. 10 through 13, and consists of a tubular member 74 having a needle 78 on one end with an opening therethrough, and a drive piston or stopper 82 in the other end. An elongated rod 84 is provided on the outer end of the drive stopper 82. A non-retractable plunger or stopper 88 in the tubular member 74, has therethrough a centrally disposed longitudinal opening 90, and is in contact with the forward end of the drive stopper 82.

BRIEF DESCRIPTION OF THE DRAWING

FIG. 1 is an elevation view of a dispensing holder 10 containing a cartridge 12 embodying the applicant's invention.

FIG. 2 is a top plan view, taken substantially on plane 2—2 in FIG. 1, showing the pivoted end of the dispensing holder 10 in an open position.

FIG. 3 is an enlarged section view, taken substantially on plane 3—3 in FIG. 2, showing structural details of the operator head 18 on the dispensing holder 10.

FIG. 4 is an elevation view of the cartridge 12 in FIG. 1, removed from the dispensing holder 10, showing the drive stopper 54 and the non-retractable stopper 58 in their initial position in the tubular member 42.

FIG. 5 is an enlarged section view, taken substantially on plane 5—5 in FIG. 4, showing the longitudinal opening 60 through the non-retractable stopper 58 and the attachment stud 56 in the drive stopper 54.

FIG. 6 is an enlarged section view, taken substantially on plane 6—6 in FIG. 4, showing structural details of the hollow needle 52 and the forward end of the cartridge 12.

FIG. 7 is a section view, taken substantially on plane 7—7 in FIG. 5, showing the central opening 60 through the non-retractable stopper 58.

FIG. 8 is an enlarged section view, similiar to FIG. 5, showing a modification of the applicant's invention.

FIG. 9 is a section view, taken substantially on plane 9—9 in FIG. 8, showing the annular array of longitudinal openings 64 through the non-retractable stopper 62, and the central reservoir 66 therein.

FIG. 10 is an elevation view of a dispensing cartridge 12 showing another modification of the applicant's invention.

FIG. 11 is a section view, taken substantially on plane 11—11 in FIG. 10, showing structural details of the dispensing cartridge.

FIG. 12 is a section view, taken substantially on plane 12—12 in FIG. 10, showing construction of the hollow needle 78 and the forward end of the dispensing cartridge 12.

FIG. 13 is a section view, taken substantially on plane 13—13 in FIG. 10, showing the laterally extending gripping fingers 80 on the tubular member 74.

FIG. 14 is a section view, similiar to FIG. 11, showing still another modification of the invention.

FIG. 15 is a section view, taken substantially on plane 15—15 in FIG. 14, showing the annular array of longitudinal openings 94 and the central reservoir 96 in the non-retractable stopper 92.

FIG. 16 is a section view, similiar to FIG. 14, showing a further modification of the applicant's invention.

FIG. 17 is a section view, similiar to FIG. 16, showing yet another modification of the applicant's invention.

FIG. 18 is a section view, taken substantially on plane 18—18, showing the annular array of longitudinal openings 110 and the central reservoir 112 in the non-retractable stopper 108.

CONSTRUCTION

Reference is made to the drawings in which numeral 10 designates injecting device and dispensing holder, of the type customarily used in the medical and nursing profession, having therein a removable cartridge 12 provided with a conventional sealed hollow needle on one end and an operator actuated means on the other end. The dispensing holder 10 comprises an elongated shell 14 having a threaded opening 16 in the forward end and a pivotally attached operator head 18 on the other end. The operator head 18 comprises a cylindrical cup 20 with a pair of longitudinal extensions 22 thereon attached to the shell 14 by diametrally disposed pintles 24.

A ring 26 on the cylindrical cup 20 has thereon two lateral gripping fingers 28. A piston 30 in the cylindrical cup 20, is held therein by a retainer ring 32, and yieldably urged to its forward position by a coil spring 34. A reciprocable plunger 36, centrally supported in the operator head 18, has a threaded opening 38 in the forward end and an operator disc 40 on the opposite end. The removable cartridge 12 comprises a tubular member 42, preferably made of glass or other transparent material, having thereon a series of graduations 44.

A cap 46, on the forward end of the tubular member 42, is provided with an external threaded section 48, and has therethrough a longitudinal axial duct 50. A sealed hollow needle 52, permanently mounted in the cap 46, communicates with the interior of the tubular member 42 through the longitudinal axial duct 50. A slidable drive stopper or piston 54 in the tubular member 42, adjacent the back end thereof, has secured therein a centrally disposed rearwardly extending threaded stud 56.

A non-retractable stopper or plunger 58, in contact with the forward end of the slidable drive piston 54 has therethrough a central by pass opening 60.

The modification of the applicant's invention disclosed in FIGS. 8 and 9 has a non-retractable stopper 62 which differs in construction from that shown in FIGS. 1 through 7. The non-retractable stopper 62 has therethrough an annular array of longitudinal by pass openings 64, and a central reservoir 66 having a discharge opening 68 in sealing engagement with the forward end of the slidable drive piston 54. A non-toxic dye or coloring agent 70 is provided in the central reservoir 66 for a purpose which will be later herein explained. In all other aspects the construction of this embodiment is identical to that disclosed in FIGS. 1 through 7.

The modification of the applicant's invention disclosed in FIGS. 10 through 13 differs from the embodiments shown in FIGS. 1 through 9, in that it is not used in conjunction with a dispensing holder 10. In this embodiment, the cartridge 12 comprises a tubular member 74, preferably made of glass or other transparent material, having on the forward end thereof a cap 76. A hollow needle 78, permanently mounted in the forward end of the cap 76, communicates with the interior of the tubular member 74.

A pair of laterally extending gripping fingers 80 are provided on the back end of the tubular member 74. A slidable drive piston 82 in the tubular member 74 has thereon an integral actuator rod 84 with an operator disc 86 on the back end. A non-retractable stopper or plunger 88, in contact with the forward end of the drive stopper 82, has therethrough a central opening 90.

The modification of the applicant's invention, disclosed in FIGS. 14 and 15, has a non-retractable stopper 92 which differs in construction from that shown in the embodiment of FIGS. 10 through 13. The non-retractable stopper 92 has therethrough an annular array of longitudinal openings 94, and a central reservoir 96 having a discharge opening 98 in sealing engagement with the forward end of the slidable drive stopper 82. A non-toxic dye or coloring agent 100 is provided in the central reservoir 96 for a purpose which will be later herein explained.

The modification of the applicant's invention disclosed in FIG. 16 has a slidable drive stopper 102 which differs in construction from that shown in the embodiments of FIGS. 10 through 15. The dlidable drive stopper 102 has a centrally disposed rearwardly extending threaded stud 104 detachably engaged with the forward end of an operator plunger 106.

The modification of the applicant's invention, disclosed in FIGS. 17 and 18 has a non-retractable stopper 108 which differs in construction from that shown in the embodiment of FIG. 16. The non-retractable stopper 108 has therethrough an annular array of longitudinal openings 110, and a central reservoir 112, having a discharge opening 114 in sealing engagement with the forward end of the slidable drive stopper 102. A non-toxic dye or coloring agent 116 is provided in the central reservoir 112 for a purpose which will be later herein explained.

The preceding discussion completes a description of the structural details of the disclosed embodiments of the applicant's invention, however, to comprehend more fully the subject matter herein presented, a discussion is immediately hereinafter directed to the manner in which the device operates to fulfill its purpose and perform its intended function.

USE AND OPERATION

A discussion of the modus operandi for the applicant's invention will be limited to the embodiments disclosed in FIGS. 1 through 9, since all of the disclosed modifications of the applicant's invention function in substantially the same manner. In practice, when it is desired to administer the medical solution in the cartridge 12 of FIG. 4, the cartridge 12 is placed in a dispensing holder 10 of the type disclosed in FIGS. 1 and 2.

This is done by swinging the operator head 18 of the dispensing holder 10 to the broken line position 120 shown in FIG. 2. The cartridge 12 is next inserted into the shell 14 and rotated to engage the threads 48 on the forward end of the cap 46 in the threaded opening 16 of the dispensing holder 10. The plunger 36 is then rotated so as to engage the stud 56 on the drive stopper 54 in the threaded opening 38 of the plunger 36.

The hollow needle 52 is inserted in the patient, and the plunger advanced, thereby moving the drive stopper 54 and the non-retractable stopper 58 forward in the tubular member 42. This forward movement of the two stoppers 54 and 58 thus forces medical solution from the cartridge 12 through the hollow needle 52 and into the patient. The graduations 44 on the tubular member enables the correct amount of medication to be administered. The hollow needle 52 is then withdrawn from the patient.

If for any reason the plunger 36 is subsequently retracted, the drive stopper 54 moves rearwardly, but the non-retractable stopper 58 remains in its advanced position, shown by the broken lines 122 in FIG. 4. Medical solution is thus drawn through the central opening 60 in the non-retractable stopper 58 to fill the space created between the two stoppers 54 and 58. This flow of medical solution into the space between the two stoppers 54 and 58 avoids the creation of a partial vacuum therebetween so as to prevent the non-retractable stopper 58 from being drawn rearwardly from its advanced position 122 in the tubular member 42.

The non-retractable stopper 58 thus serves as a visual indicator showing the exact amount of medical solution which has been ejected from the cartridge 12. More importantly, however, if the two stoppers 54 and 58 are separated, it also serves as a warning that the medical solution in the cartridge 12 may have been diluted, modified or substantially changed from that which was originally provided by the manufacturer.

In the modification shown in FIGS. 8 and 9, the non-retractable stopper 62 is driven forwardly in the tubular member 52 by the drive stopper 54 in precisely the manner described in the discussion of the embodiment shown in FIGS. 1 through 7. However, when the plunger 36 is retracted, the drive stopper 54 is drawn out of sealing engagement with the non-retractable stopper 58 thereby uncovering the discharge opening 68 of the central reservoir 66.

The non-toxic dye or coloring agent 70 in the central reservoir 66 is thus permitted to flow into the space between the two stoppers 54 and 62 so as to discolor the medical solution drawn rearwardly through the annular array of spaced openings 64 in the non-retractable stopper 62. This affords an additional visual warning that the original medical solution in the cartridge 12 supplied by the manufacturer may have been altered.

Based upon the foregoing discussion, the applicant is of the opinion that her invention has fulfilled a long-felt need in the field of injection devices for medical solutions, and that she has made a valuable and significant contribution to the related art. However, while the invention was described with reference to the structural details of a limited number of embodiments, the principles involved are susceptible of numerous other practical adaptations.

Therefore, I claim as new and desire to secure by Letters Patent:

1. An injecting device for medical solutions comprising a sealed cylindrical tubular medicament receiving and dispensing barrel member having indicia means thereon and including a needle means on one end and an acutating means on the other end, said actuating means having a sliding fluid tight drive piston thereon and received in the inside of said barrel member and positioned adjacent said other end, a medicament cavity in said barrel extending from said one barrel end toward said other end of said barrel, a means for indicating the quantity of medicament in said barrel cavity comprising a snug fitting plunger means also slidingly received in said barrel means with one end abutting but unattached to said piston and the other end facing said medicament cavity, said snug fitting plunger means having at least one longitudinally extending fluid by pass hole therethrough and defining a non-retractable plunger stopper whereby pressure by the piston on said non-retractable plunger aspirates residual medicament in said cavity and the non-retractable plunger stopper will remain in a fixed position in the barrel so that the indicia will indicate the position of the plunger and residual quantity of medicament is remaining in the barrel cavity.

2. The injecting device of claim 1 wherein the tubular barrel is a cartridge and is received in a dispensing holder and the said actuating means is a threaded stud for detachable connection to a movable operator disc on the dispensing holder.

3. The device of claim 1 wherein the said at least one by pass hole is located away from the center of said plunger and comprises several spaced longitudinally holes.

4. The injecting device for medical solutions described in claim 1 in which the piston plunger is detachably connected to the actuating means.

5. The injecting device for medical solutions described in claim 1 having in addition thereto: a reservoir in the non-retractable plunger having a discharge opening in sealing engagement with the forward end of the drive piston, and a non-toxic dye in the reservoir which escapes and discolors the medical solution that is drawn into the space between the two stoppers through the longitudinal opening in the non-retractable plunger when the drive piston is retracted by the actuating means.

* * * * *